US010429366B2

(12) United States Patent
Gamache

(10) Patent No.: US 10,429,366 B2
(45) Date of Patent: Oct. 1, 2019

(54) METHODS AND SYSTEMS FOR DETECTION OF NON-VOLATILE SOLUTES

(71) Applicant: DIONEX CORPORATION, Sunnyvale, CA (US)

(72) Inventor: Paul H. Gamache, Hudson, NH (US)

(73) Assignee: Dionex Corporation, Sunnyvale, CA (US)

( * ) Notice: Subject to any disclaimer, the term of this patent is extended or adjusted under 35 U.S.C. 154(b) by 471 days.

(21) Appl. No.: 15/189,798

(22) Filed: Jun. 22, 2016

(65) Prior Publication Data

US 2016/0377582 A1 Dec. 29, 2016

Related U.S. Application Data

(60) Provisional application No. 62/183,621, filed on Jun. 23, 2015.

(51) Int. Cl.
*G01N 30/34* (2006.01)
*G01N 30/88* (2006.01)

(52) U.S. Cl.
CPC ............. *G01N 30/88* (2013.01); *G01N 30/34* (2013.01)

(58) Field of Classification Search
CPC ...................................................... G01N 30/34
See application file for complete search history.

(56) References Cited

U.S. PATENT DOCUMENTS

| | | | | |
|---|---|---|---|---|
| 4,629,478 A * | 12/1986 | Browner | B01F 3/04007 239/434 |
| 5,026,994 A | 6/1991 | Westcott et al. | |
| 5,098,657 A | 3/1992 | Blackford et al. | |
| 5,247,842 A | 9/1993 | Kaufman et al. | |

(Continued)

FOREIGN PATENT DOCUMENTS

| | | |
|---|---|---|
| CN | 103354898 A | 10/2013 |
| EP | 1739720 A2 | 1/2007 |
| GB | 2499681 B | 2/2016 |

OTHER PUBLICATIONS

Cohen et al., "Advances in Aerosol-Based Detectors", Adv Chromatogr. 2014, 52, pp. 1-53.

(Continued)

*Primary Examiner* — Lisa M Caputo
*Assistant Examiner* — Alex T Devito
(74) *Attorney, Agent, or Firm* — Thomas F. Cooney

(57) ABSTRACT

A system for detection of non-volatile solutes dissolved in solution comprises: a spray emitter system configured to receive a flow of the solution and generate an aerosol comprising droplets thereof, the generated droplets comprising a restricted size range; a spray chamber configured to receive the aerosol and emit a modified aerosol comprising droplets having a diameter smaller than a predetermined value; a conduit configured to receive a flow of the modified aerosol and to evaporate the solvent so as to generate an aerosol comprising solid particles of the solutes; a charging chamber configured to receive the aerosol and impart electric charge to the solid particles; and a detector configured to measure a quantity of charge imparted to the solid particles, wherein the restricted size range is such that solid particles having diameters greater than 10 nm comprise a substantial portion of all particles received by the charging chamber.

23 Claims, 10 Drawing Sheets

(56) References Cited

U.S. PATENT DOCUMENTS

| | | | | |
|---|---|---|---|---|
| 5,381,701 | A | 1/1995 | Frankenthal et al. | |
| 6,153,123 | A * | 11/2000 | Hampden-Smith | B01J 2/003 106/31.14 |
| 6,544,484 | B1 | 4/2003 | Kaufman et al. | |
| 6,568,245 | B2 | 5/2003 | Kaufman | |
| 7,777,868 | B2 | 8/2010 | Blackford et al. | |
| 7,796,727 | B1 | 9/2010 | Kaufman | |
| 7,812,306 | B2 | 10/2010 | Fissan et al. | |
| 7,969,711 | B2 | 6/2011 | Prymak et al. | |
| 8,115,930 | B2 | 2/2012 | Anderson, Jr. et al. | |
| 8,573,404 | B2 | 11/2013 | McNeil-Watson | |
| 9,506,843 | B2 | 11/2016 | Peters et al. | |
| 2003/0202920 | A1 | 10/2003 | Kaufman et al. | |
| 2009/0250608 | A1 * | 10/2009 | Mordehai | H01J 49/167 250/288 |
| 2011/0220811 | A1 | 9/2011 | Dick et al. | |
| 2013/0265574 | A1 | 10/2013 | Buckley et al. | |
| 2014/0352411 | A1 | 12/2014 | Yim et al. | |

OTHER PUBLICATIONS

Dixon, et al., “Development and Testing of a Detection Method for Liquid Chromatography Based on Aerosol Charging”, Anal. Chem. 2002, 74, pp. 2930-2937.

Hutchinson et al., “Universal response model for a corona charged aerosol detector”, Journal of Chromatography A, 1217 (2010), pp. 7418-7427.

Kahen et al., “Modified Nukiyama-Tanasawa and Rizk-Lefebvre models to predict droplet size for microconcentric nebulizers with aqueous and organic solvents”, J. Anal. At. Spectrom, 2005, 20, pp. 631-637.

Leonard F. Pease III, “Physical analysis of virus particles using electrospray differential mobility analysis”, Trends in Biotechnology, 2012, vol. 30, (4), pp. 216-224.

Liu et al., “On the Performance of the Electrical Aerosol Analyzer”, J. Aerosol Science, 1975, vol. 6, pp. 249-264.

McCarthy et al., “HPLC Analysis of Nonvolatile Analytes Using ChargedAerosol Detection”, LCGC North America, 2005, vol. 23, (2), pp. 150-161, http://www.chromatographyonline.com/hplc-analysis-nonvolatile-analytes-using-charged-aerosol-detection.

Robert A. Moreau, “The Analysis of Lipids via HPLC with a Charged Aerosol Detector”, Lipids, (2006), vol. 41, (7), pp. 727-734.

Sinclair et al., “Charged Aerosol Detection: Factors for consideration in its use as a generic quantitative detector”, Chromatography Today, 2008, vol. 1.3, pp. 5-9.

Stolywho, et al., “Analysis of Triglycerides in Oils and Fats by LiquidChromatography with the Laser Light Scattering Detector”, Anal. Chem. 1985, 57, pp. 1342-1354.

Swartz et al., “Charged Aerosol Detection in Pharmaceutical Analysis: An Overview”, LCGC, Special Issues (2009), vol. 27, Issue 4, pp. 40-48, http://www.chromatographyonline.com/charged-aerosol-detection-pharmaceutical-analysis-overview.

Ude et al., “Aerosol size standards in the nanometer size range—II. Narrow size distributions of polystyrene 3-11 nm in diameter”, Journal of Colloid and Interface Science 293 (2006), pp. 384-393.

Vehovec, et al., “Review of operating principle and applications of the charged aerosol detector”, Journal of Chromatography A, 1217 (2010) pp. 1549-1556.

Agilent-Varian, “Universal quantification using ELS detection and real-time response control”, Application Note SI-01722, 2008, http://www.chromatographyonline.com/e-separation-solutions-09-10-2008, pp. 1-3.

Gamache et al., “HPLC Analysis of Nonvolatile Analytes Using Charged Aerosol Detection”, LCGC North America, 2005, vol. 23 (2), pp. 151-161.

Matsuyama et al., “Effects of Densities of Brominated Flame Retardants on the Detection Response for HPLC Analysis with a Corona-charged Aerosol Detector”, Analytical Sciences 2015, vol. 31, pp. 61-65.

Pui et al., “Experimental Study of Particle Deposition in Bends of Circular Cross Section”, Aerosol Science and Technology (1987), 7:301-315.

* cited by examiner

METHODS AND SYSTEMS FOR DETECTION OF NON-VOLATILE SOLUTES

CROSS REFERENCE TO RELATED APPLICATIONS

This application claims priority to U.S. Provisional Application No. 62/183,621 titled "Methods and Systems for Detection of Non-Volatile Solutes" and filed on Jun. 23, 2015 and, further, is related to commonly-assigned co-pending U.S. patent application Ser. No. 14/288,693, filed May 28, 2014 and titled "Nebulizer for Charged Aerosol Detection (CAD) System", said applications hereby incorporated by reference herein in their entirety.

FIELD OF THE INVENTION

The present invention relates to devices for detecting and quantifying components of a liquid sample stream.

BACKGROUND OF THE INVENTION

Charged aerosol detection is a popular and valuable technique for the detection and quantification of substances present in a liquid sample stream, and is particularly well-suited to use in connection with liquid chromatography applications. Briefly described, a charged aerosol detection (CAD) system consists of a nebulizer for generating a spray of droplets from a liquid sample stream (for example, the effluent from a chromatographic column), a discharge source for selectively charging the nonvolatile residue particles produced by drying the droplet spray, and a collector, where the aggregate charge imparted to the particles is measured using an electrometer. The resultant signal is in direct proportion to the quantity of analyte present and is representative of the concentration of the nonvolatile components of the sample stream. The CAD technique is sometimes referred to as a "universal" detection technique, as it is capable of quantifying a wide variety of nonvolatile substances with consistent response. Further details regarding the design, operation and advantages of CAD systems are set forth in U.S. Pat. No. 6,568,245 by Kaufman ("Evaporative Electrical Detector"), the disclosure of which is incorporated herein by reference.

A CAD system may be advantageously coupled as a detector to a High-Performance Liquid Chromatography (HPLC) system or other Liquid Chromatography (LC) system. The information provided by such a LC-CAD system is fundamentally different from that provided by LC systems employing other commonly used detectors (such as mass spectrometers) or UV-visible detectors) in that the CAD detection principle involves the measuring of charged solid aerosol particles that have a selected range of mobility rather than the measuring of individual gas-phase ions that are differentiated based upon m/z or analytes in solution that are differentiated based on optical absorption or fluorescence. Accordingly, CAD technology is able to quantify all analyte particles that acquire charge, including those that cannot ionize or do not have chromophores. It has been shown (R. C. Flagan, Aerosol Sci. Technol. 28, 1998)) that the signal obtained using CAD technology depends primarily upon particle size across a wide range and does not depend significantly upon individual analyte properties, such as chemical composition or chemical structure. The result is accurate and consistent response, regardless of analyte structure. Using charged aerosol detection, it is possible to measure any nonvolatile and most semivolatile analytes. A similar HPLC detection method, termed aerosol charge detection, has been described by R. W. Dixon and D. S. Peterson (Anal. Chem. 74, 2930-2937, 2002). The CAD technique can complement atmospheric pressure ionization MS techniques such as electrospray and APCI.

A schematic diagram of a conventional CAD device is shown in FIG. 1. The detection method includes pneumatic nebulization, at a nebulizer, of eluate received from an HPLC column 2 so as to create droplets 3. In known fashion, the HPLC column is fluidically coupled to and receives a sample liquid from an HPLC system 19 that may comprise several other components, such as one or more solvent supplies, injector valves, gradient valves for mixing solvents in controlled variable proportions, etc. The nebulizer may include a spray emitter 1 configured to break up a liquid into a spray of droplets and a spray chamber 17 configured to receive the spray of droplets and cause evaporation of volatile substances such that only dried particles 6, comprising non-volatile analytes, remain. A gas inlet 7 provides a flow of gas that is divided at a gas-splitting junction 8 into a flow 9*a* of nebulizing gas that is provided to the spray emitter 1 through a first gas conduit 34*a* and a flow 9*b* of reagent gas that is provided to a charging chamber 11 through a second gas conduit 34*b* that causes the reagent gas to flow past an ionization source 10, such as a corona needle before entering the charging chamber 11. If the ionization source 10 comprises a corona needle, the corona needle is maintained, during operation, at a high applied voltage by voltage supply 35.

The spray emitter 1 of the conventional CAD device shown in FIG. 1 is configured such that the flow of nebulizing gas is introduced at an approximately right angle relative to the direction of flow of liquid into the nebulizer and such that the generated droplets are caused to collide at high velocity with the surface of an impactor 4. The largest of the initial droplets 3 are broken up into smaller droplets upon collision with the impactor 4 and the resulting small droplets remain entrained in a portion of the nebulizing gas flow along a path through a conduit 18. Any remaining large droplets or droplets that are too large to be entrained in the gas flow into conduit 18 are directed to waste via a drain port 5. The droplets passing through conduit 18 undergo ambient-temperature solvent evaporation so as to yield an aerosol of analyte solid particles 6 suspended in the gas flow 9*a*. A turbulent jet of positive ions 12, formed by passing the reagent gas stream 9*b* past the ionization source and through an orifice, is mixed, in a charging chamber 11, with the opposing-flow stream of analyte aerosol particles 6. In this process, charge is transferred diffusionally to analyte particles. Excess positive ions and smaller, high mobility, negatively and positively charged particles are trapped or neutralized by a weak electric field applied by electrode 16 and the charged analyte particles 13 impinge on a conductive filter 14, which transfers the charge to an electrometer 15 for signal transduction.

The response curve for CAD and other aerosol detectors is often described by the following equation:

$$S=a[\text{Amount}]^b \quad \text{Eq. 1}$$

in which S represents observed signal (e.g., fA $m^3$ $\text{particles}^{-1}$) and where the pre-exponential coefficient (a) indicates absolute sensitivity and the exponent (b), referred to herein as the power law, describes the shape of the response curve. At any point on a response curve, sensitivity can be described by the slope of the curve:

$$a=S/[\text{Amount}] \quad \text{Eq. 2}$$

In practice, b≠1, sensitivity changes as a function of analyte amount and the instrument response is therefore non-linear.

Dixon and Peterson ("Development and testing of a detection method for liquid chromatography based on aerosol charging." Analytical chemistry 74(13), 2002, pp. 2930-2937) describe that:

$$D_p = D_d (C/\rho)^{1/3} \quad \text{Eq. 3}$$

in which $D_p$=dried particle diameter, $D_d$=initial droplet diameter C=droplet residue concentration, and ρ is the density of the particle. Thus, the average particle size increases with the amount of particle-forming analytes in the original sample. Dixon and Peterson further describe that:

$$S = 1.61\times10^{-10} D_p^{1.11} \text{ (for } D_p > 10 \text{ nm)} \quad \text{Eq. 4a}$$

$$S = 2.30\times10^{-16} D_p^{6.6} \text{ (for } D_p \leq 10 \text{ nm)} \quad \text{Eq. 4b}$$

The above equations show that the signal response of CAD is intrinsically non-linear. The non-linearity is most evident in experimental results spanning a wide dynamic range. Cohen and Liu ("1 Advances in Aerosol." Advances in chromatography 52, 2014)) state that "All aerosol-based detectors exhibit a nonlinear response over large concentration ranges, and this is a major limitation for these detectors seeing greater use." Likewise, Hutchinson et al ("Universal response model for a corona charged aerosol detector." Journal of Chromatography A 1217(47), 2010, pp. 7418-7427) state that "A significant barrier to the implementation of the aerosol detectors has been that they exhibit non-linear calibration curves." Combination of Eq. 3 with Eq. 4a predicts that, for sufficiently large analyte particles, the signal, S, should obey an overall approximately ⅓ power law with concentration as the multiplicative product of individual power laws of ⅓ and 1.11. A power law response has been observed in various experimental results (i.e., FIGS. 9-12) set forth in U.S. Pat. No. 6,568,245 in the name of inventor Kaufman. Accordingly, experimental results illustrated in that patent represent the detector signal (current) raised to the 3rd power so as to approximate a linear response. However, the same patent also states that "In actual practice . . . detector electrical current has been found to vary more closely in proportion to the square-root of the concentration rather than the cube-root. This may be caused by coagulation in the aerosol, effects of analyte concentration on nebulizer performance, or other factors presently unknown."

Such non-linear response is commonly viewed as the single most significant limitation of LC-aerosol detectors. Further, solvent dependency of response during solvent gradient LC separations is often considered to be an almost equally significant limitation. Solvent dependency mainly refers to changes in response attributed to changes in primary aerosol characteristics, transport and evaporation. The main solvent properties of interest are surface tension, viscosity and density. An important consideration is solvent load especially for water since, except for very low liquid flow rates, the aerosol is expected to be supersaturated with water vapor.

SUMMARY OF THE INVENTION

Numerous direct comparison studies have been performed in the inventor's laboratory so as to compare the performance of the conventional nebulizer (having a flow of nebulizing gas at right angles to the flow of liquid and an impactor) with that of a newly developed nebulizer (using parallel gas/liquid flow as described in more detail below and in co-pending U.S. patent application Ser. No. 14/288,693). The results of these studies have indicated that the conventional design consistently exhibits a higher power law for low analyte levels (greater deviation from ⅓) than does the newly developed design. The inventor considers that the greater deviation from predicted behavior is likely attributable to droplet-impactor collisions in the conventional CAD nebulizer, which reduce droplet size distribution leading to detection of a higher proportion of smaller particles (smaller than 10 nm diameter) than are observed using the new design. Thus, the inventor has concluded that particles of $D_p$<10 nm may contribute more substantially to CAD signal, and therefore to the observed behavior of Signal versus concentration, than what is apparently recognized in prior art.

The coefficients in Eqs. 4a and 4b indicate that absolute sensitivity for $D_p$<10 nm is lower than that for $D_p$>10 nm. Therefore, in order for particles of $D_p$<10 nm to modify the ~⅓ power law behavior of CAD signal versus concentration measurements, the inventor concludes that their instantaneous concentration (particles/$m^3$) within the aerosol must be several orders of magnitude higher than that of the larger particles.

The inventor has performed new model calculations (not shown) using the above equations and a theroretical model for concentric nebulization (as described below and in co-pending U.S. patent application Ser. No. 14/288,693) that includes the fluid properties of typical LC solvents, liquid and gas flow rates, chromatographic band volumes and within-band solute distribution. These new calculations as well as experimental results (see FIGS. 9A-9B) strongly support a substantial contribution to signal from particles of <10 nm diameter using current CAD designs. The new calculations predict an initial polydisperse primary aerosol (e.g., log-normal size distribution) as well as subsequent preferential transport of smaller fluid droplets which, by Eq. 3, leads to preferential detection of smaller dried particles. Eq. 3 also shows that the fraction of signal contributed from the smallest particles should be greatest for low injected analyte amounts (e.g., low analyte concentrations in a sample) and, for a given injection, greatest toward the outer portions of each solute band (i.e., chromatographic peak).

Given the above calculation results and arguments indicating the possible significant influence of particles of $D_p$≤10 nm on the overall power law, it is expected that, using current CAD instrument designs, the power law of CAD may therefore change throughout the dynamic range in a fashion such that the exponent, b, is greatest for low analyte amounts and also toward the edges of a chromatographic peak. Accordingly, using current CAD instrument designs, the power law exponent, b, is expected to approach a minimum of ~⅓ for high analyte amounts and toward the center of a chromatographic peak. Such 'gradients' in power law as a function of analyte amount and across a chromatographic solute band are evident in experimental data that includes various analytical conditions and design iterations of LC-CAD.

Based on the inventor's new insight, as described above, the present teachings provide new CAD instrument design concepts to minimize the contribution, to the CAD signal, of dried particles for which $D_p$≤10 nm. Implementation of the new design concepts can provide an instrument response that approaches a ⅓ power law response over a wider dynamic range than is currently achieved. The new designs can thus provide a wider linear dynamic range (when the instantaneous signal is raised to the third power). Achieving this goal would thereby remove or greatly minimize a major limitation to the usefulness of CAD.

Accordingly, the present teachings describe new CAD instrument design improvements. Various instrument embodiments in accordance with the present teachnings may include various design features that address or correspond to one or both of the following processes: (1) using spray generation parameters (e.g., orifice diameter/geometry, nebulizing gas velocity and volumetric flow rate) that, for a given combination of inlet liquid flow rate, liquid surface tension, liquid viscosity and liquid density produce a primary droplet size distribution which, upon evaporation, results in relatively small numbers of ≤10 nm dried particles; and (2) using transport conditions (e.g., gas velocities, path geometries, evaporation temperature, etc) to maximize transport of droplets of sizes (diameters) that are sufficiently small to permit complete liquid evaporation but that are also sufficiently large such that, upon evaporation, the resulting dried particles are of >10 nm diameter. Also, design features are described that may be employed to suppress secondary atomization of droplets and transport of oppositely-charged particles to the detector resulting from electrospray-like surface charge accumulation on droplets. However, such natural spray electrification is believed to not pose a significant problem for particle detection, in most instances.

Various embodiments of apparatuses, systems and methods in accordance with the present teachings may address or implement the above-noted process (1) through the provision of means for introducing a flow of a nebulizing gas into a spray chamber at a spray emitter tip and separately introducing a separate flow of a sheath gas into the spray chamber at the spray emitter tip, where the nebulizing gas flow is introduced parallel to the flow of an inlet sample liquid and the sheath gas flow is introduced either parallel to the flow of the inlet sample liquid or at an angle, relative to the flow of the inlet sample liquid, that is less than ninety degrees and where the nebulizing gas is introduced closer to the flow of the inlet sample liquid than is the sheath gas. In various embodiments, the inlet sample liquid flow is introduced by a capillary, the nebulizing gas flow is introduced by one or more nebulizing gas conduits surrounding or exterior to the capillary and the sheath gas flow is introduced by one or more conduits surrounding or exterior to the one or more nebulizing gas flow conduits. According to some embodiments, the inlet sample liquid flow is introduced at the spray emitter tip by a capillary, the nebulizing gas flow is introduced by a single nebulizing gas conduit concentrically surrounding the capillary at the spray emitter tip and the sheath gas flow is introduced by a single sheath gas conduit surrounding the nebulizing gas conduit at the spray emitter tip. According to some alternative embodiments, the sheath gas is introduced into the spray chamber by one or more sheath gas capillaries or tubes that are separate from the spray emitter and are disposed so as to introduce the sheath gas at an angle, relative to the flow of the inlet sample liquid, that is less than ninety degrees.

In various embodiments, the flows of nebulizing gas and sheath gas may be separately controlled, possibly automatically, such that the size of droplets formed at the spray emitter tip is determined by the flow rate of the nebulizing gas and such that the combined flow rates of the nebulizing gas and sheath gas are constant. The relative proportions of the flows of the nebulizing and sheath gasses may be controlled so as to vary in accordance with a varying tendency of the sample liquid to break into droplets at the spray emitter tip, where such tendency varies in accordance with varying liquid composition during the providing of the liquid from a chromatographic column during a gradient elution. The nebulizing and sheath gasses may comprise the same or different compositions. If the nebulizing and sheath gasses are of the same composition and provided from a single gas source, then a variable flow splitter, such as a proportional valve, may be disposed between the gas source and the gas flow so as to divide a single gas flow provided by the gas source into separate nebulizing gas and sheath gas portions.

Various embodiments of apparatuses, systems and methods in accordance with the present teachings may address the process of natural spray electrification through the provision of means for neutralizing charge imparted to droplets during their formation at a spray emitter tip that introduces the droplets into a spray chamber. The means for neutralizing charge may be provided in the form of one or more of an corona needle that is energized by a voltage source, a radioactive emitter of either α-particles or β-particles or an X-ray emitter positioned within the spray chamber proximate to the spray emitter tip and configured to generate a sufficient number of gaseous ions within the gas surrounding the droplets so as to neutralize any charge acquired by the droplets during their formation. If the means for neutralizing charge is provided as a corona needle, then an alternating current (AC) voltage may be applied to the needle so as to alternately generate positive and negative ions in the gas within the spray chamber that can neutralize droplets charged with either negative or positive polarity, respectively. The quantity of ions generated within the spray chamber by the means for neutralizing charge may be adjusted by adjustment of the position of the corona needle or α-particle, β-particle, or X-ray emitter or by adjustment of the voltage applied to a corona needle. The adjustment of the generated quantity of ions may be calibrated by adjusting one or more of these parameters so as to minimize a signal baseline while operating a CAD instrument in the absence of application of charge to dried particles.

Various embodiments of apparatuses, systems and methods in accordance with the present teachings may address or implement the above-noted process (3), in part, by configuring a spray chamber of a CAD system with an internal chamber shape such that the largest droplets (which are incapable of complete solvent evaporation during transport through the system) are directed along a first path that leads to a waste port whereas smaller droplets are directed along a second path, divergent from the first path, that leads to a particle charging chamber, wherein the walls of the spray chamber are oriented so as to minimize breaking apart of droplets upon impact with the walls. The above-noted process (3) may be further addressed or implemented, in part, by configuring the CAD system such that a transport conduit provides a straight flow path or only low angle bends where the radius of curvature of the bend is at least 5 (five) times the cylindrical tube radius of the transport conduit (e.g., Pui, D. Y. H. et al. "Experimental Study of Particle Deposition in Bends of Circular Cross Section", Aerosol Science and Technology, 7:3, 1987, pp. 301-315) between the spray chamber and the downstream charging chamber such that impact of droplets against the walls of the transport conduit is minimized.

If the spray chamber is of a design which at least partially reverses the trajectory of the droplets to be introduced into the transport conduit, relative to the trajectory of droplets formed at the spray emitter tip, then the outlet port of the spray chamber may be disposed such that, after such trajectory reversal, the flow of gas and entrained droplets does not encounter any additional trajectory changes within the spray chamber and does not encounter at a high angle to any surfaces within the spray chamber or outlet port. If smaller droplets, whose total evaporation would yield particles of diameter that is <10 nm, remain entrained within the gas flow, either within the spray chamber or within the transport conduit, these may be removed by placement of an appropriate diffusion screen or screens within the flow path, either within the spray chamber or the transport conduit. Also, the distance between the emitter tip and the "back wall" of the spray chamber (the wall towards which the spray is initially emitted) may be configured (increased or decreased) so as to control the degree or amount of droplet solvent evaporation such that a greater or lesser number of total droplets can negotiate a reversal of trajectory. The distance may be derived based on the axial velocity of the aerosol (defined by the spray chamber dimensions and volumetric gas flow rate) and the droplet evaporation time ($t_d$), which may be estimated by:

$$t_d = \frac{\Delta H_v \rho r_i^2}{2Mk_f\Delta T} \quad \text{Eq. 5}$$

where $\Delta H_v$ is the latent heat of vaporization; p is the droplet density; $r_i$ is the initial droplet radius; M is the molecular weight of the droplet solvent; $k_f$ is the thermal conductivity of the gas film surrounding the droplets and $\Delta T$ is the difference between the gas temperature and the droplet surface temperature (Charlesworth, J. "Evaporative Analyzer as a Mass Detector for Liquid Chromatography." Anal. Chem 50:11, 1978, pp. 1414-1420).

In accordance with some embodiments, additional design features may be provided so as to address the above described limitation of CAD with respect to solvent dependency of response. As discussed above, changes in response during solvent gradient LC separations are mainly attributed to changes in solvent properties that affect primary aerosol characteristics, transport and evaporation. Accordingly, an embodiment may include real time adjustment of nebulizing gas flow according to changes in solvent properties so as to minimize changes in primary aerosol characteristics. In this regard, nebulizing gas flow adjustments may be pre-programmed based on prior knowledge of solvent properties such as viscosity, surface tension and density and using experimentally determined relationships between such properties and experimental results or, possibly, predictive models of nebulization. Furthermore, sheath gas flow may also be adjusted in real time so as to maintain a constant combined gas flow, comprised of nebulizing and sheath gas flows, so as to also minimize changes in aerosol transport and evaporation that may result from solvent gradients.

An important consideration is solvent load especially for water since, except for very low liquid flow rates, the aerosol is expected to be supersaturated with water vapor. As discussed above, under most LC conditions, some of the largest droplets must be removed to allow complete solvent evaporation. Nonetheless, even with the largest droplets removed, some solvent compositions may be such that, under the prevailing gas flow rates, some of the largest remaining droplets may fail to completely evaporate in the time available between droplet generation and introduction of the gas and particle stream into a downstream particle charging chamber. Evaporation temperature setting is one parameter that can effect evaporation time. Accordingly, some embodiments in accordance with the present teachings may include variable temperature control within the spray chamber or within a transport conduit fluidically coupled between the spray chamber and a particle charging chamber. The temperature adjustments, which may be automatically controlled, may be caused to vary in accordance with a measured or predicted varying vapor pressure, within the spray chamber, of a solvent component. Alternatively or additionally, some embodiments in accordance with the present teachings may include a liquid flow splitter (such as valve or T-junction) fluidically coupled between the source of the varying composition liquid (e.g., a chromatographic column) and the spray chamber, such that the splitter only admits a limited flow rate of liquid into the spray emitter such that the interior of the spray chamber never becomes supersaturated in any volatile component. Experiments performed by the inventor have indicated that a liquid flow split is necessary, in practice, to allow normalization of response for different solvents. Other alternative embodiments may include use of a single nebulizer-to-sheath flow ratio setting and real time adjustment of nebulizer and sheath gas flows during a run such that the total gas flow is sufficient to prevent supersaturation of any volatile component within the spray chamber.

In accordance with a first aspect of the present teachings, a system for detection and measurement of non-volatile solutes dissolved in a liquid solvent is provided, the system comprising: a spray emitter system configured to receive a flow of liquid solution comprising the solvent and dissolved solutes and to generate an aerosol comprising droplets of the liquid solution, wherein the generated droplets comprise a restricted size range; a spray chamber configured to receive the aerosol and to emit a modified aerosol consisting essentially of the carrier gas and liquid droplets having a diameter smaller than a predetermined value; a conduit configured to receive a flow of the modified aerosol from the spray chamber and to cause evaporation of the solvent from the received liquid droplets so as to generate a further modified aerosol consisting essentially of the carrier gas and solid particles of the non-volatile solutes; a charging chamber configured to receive the further modified aerosol from the conduit and to impart electric charge to the solid particles thereof; and a detector configured to receive the charged solid particles from the charging chamber and to measure a quantity of charge imparted to the solid particles, wherein the droplet restricted size range is such that particles having diameters greater than 10 nm comprise more than a predetermined percentage of all particles received by the charging chamber.

In accordance with another aspect of the present teachings, there is provided method for detecting and measuring non-volatile solutes dissolved in a liquid solution comprising a liquid solvent, the method comprising: generating an aerosol of droplets of the liquid solution, wherein the generated droplets comprise a restricted size range; transporting a portion of the droplets through one or more conduits such that collision-induced division of the non-removed droplets into smaller droplets within the one or more conduits is inhibited and such that the solvent evaporates during the transporting so as to generate a solid particle from each respective droplet of the portion of droplets; imparting electric charge to the solid particles; and measuring a quantity of charge imparted to the solid particles, wherein the droplet restricted size range and the inhibition of droplet division are such that particles having diameters greater than 10 nm comprise more than a predetermined percentage of all particles received by the charging chamber.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-3, 4A, 4B, and 5-8, 9A and 9B taken in conjunction with the following description.

Figure 2:
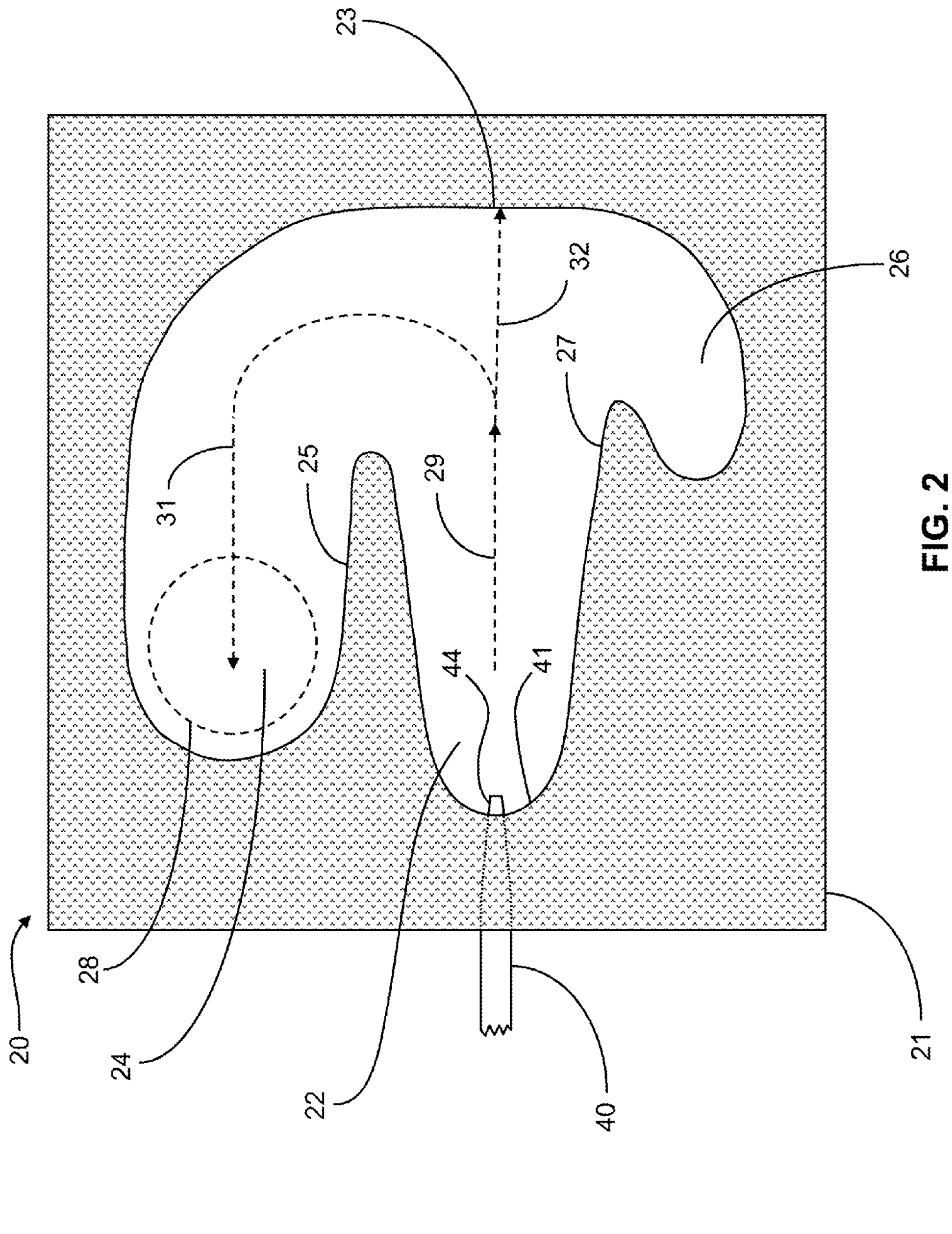
FIG. 2 is a is an elevational cross-sectional view of a CAD system nebulizer depicting the interior of a spray chamber body.

FIG. 2 depicts a cross-sectional view through a nebulizer constructed in accordance with an embodiment of an invention taught in co-pending U.S. patent application Ser. No. 14/288,693, which is assigned to the applicant of the present invention and which is published as U.S. Pre-Grant Publ. No. 2014/0352411 A1. The nebulizer 20 depicted in FIG. 2 includes a spray chamber body 21 having a central region 22 into which sample spray is introduced by means of a spray emitter 40, which is positioned within a central region 22 penetrating the front wall 41. The tip of emitter 40 is horizontally spaced from (note: the terms "horizontal", "vertical" and their variants are used herein for ease of explanation, and should not be construed as limiting the spray chamber to any particular orientation) and positioned in opposition to a medial portion (alternatively referred to herein as the "rear surface") of back wall 23. The spray chamber further includes an upper region 24 partially divided from central region 22 by means of a horizontally projecting rib or partition 25, and a lower region 26 partially divided from central region 22 by means of a horizontally projecting rib or partition 27.

Figure 3:
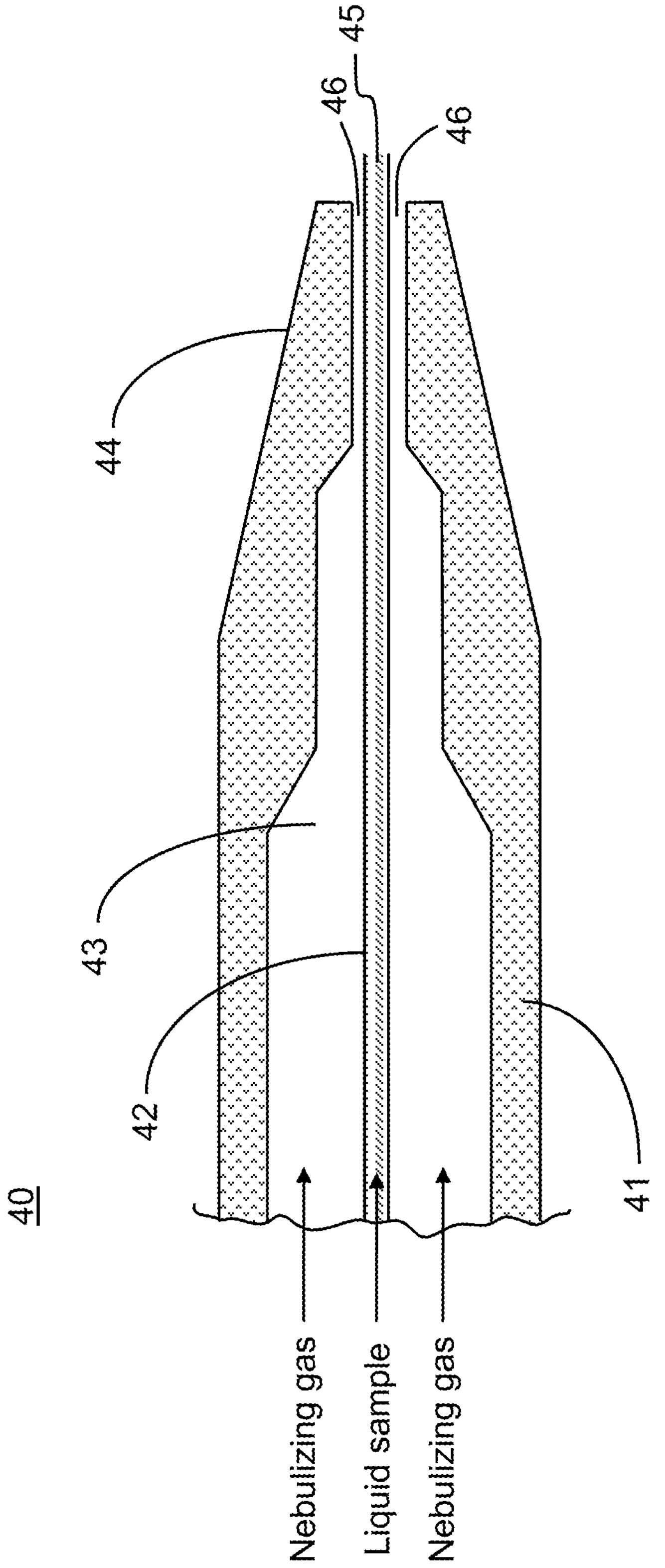
FIG. 3 is a partial cross-sectional view of a spray emitter of a CAD system nebulizer.

FIG. 3 depicts an example of a spray emitter 40 as taught in the aforementioned co-pending U.S. patent application Ser. No. 14/288,693. The spray emitter 40 may take the form of a pneumatic emitter of the type used in atmospheric pressure chemical ionization (APCI) sources for mass spectrometers. Spray emitter 40 is provided with a central passageway through which the liquid sample flows from an inlet end to an exit end of emitter 40. The central passageway may be defined interiorly of a capillary 42 extending longitudinally through the spray emitter body 41. As discussed above, the liquid sample may be the effluent of a chromatographic column, which operates to separate solutes or groups of solutes within the sample such that different solutes are introduced into the nebulizer at different times. Spray emitter 40 is further provided with one or more gas passageways 43, arranged around the central passageway, through which a nebulizing gas flow is directed. The gas will typically be supplied from a source of compressed gas, e.g., a bottle of compressed air or nitrogen.

Spray emitter 40 terminates in a nozzle 44, at which the liquid and gas flows pass into the interior of spray chamber 21 to form a droplet spray. In certain implementations of spray emitter 40, the liquid and gas flows may exit the emitter nozzle through separate orifices (depicted as 45 and 46, respectively) and interact thereafter within the spray chamber 21 to form the spray cone; the gas passageway orifice(s) may consist, for example, of a continuous annular orifice circumscribing the liquid sample orifice (as shown in FIG. 3), or a plurality of discrete orifices disposed radially around the liquid sample orifice. The gas passageway and liquid orifices are sized to optimize spray and other operational characteristics: the liquid orifice should be sufficiently small to produce droplets of relatively small diameters, but excessively small orifice sizes that are prone to frequent clogging and/or require unacceptably high pressures at the emitter inlet should be avoided; the gas orifice(s) should be sized to establish shear forces at and near the nozzle tip sufficient to produce a high-quality, stable spray of uniformly small droplets. In other implementations, the liquid and gas flows may be mixed within a chamber interior to the nozzle and exit the nozzle tip via a common orifice.

Figure 1:
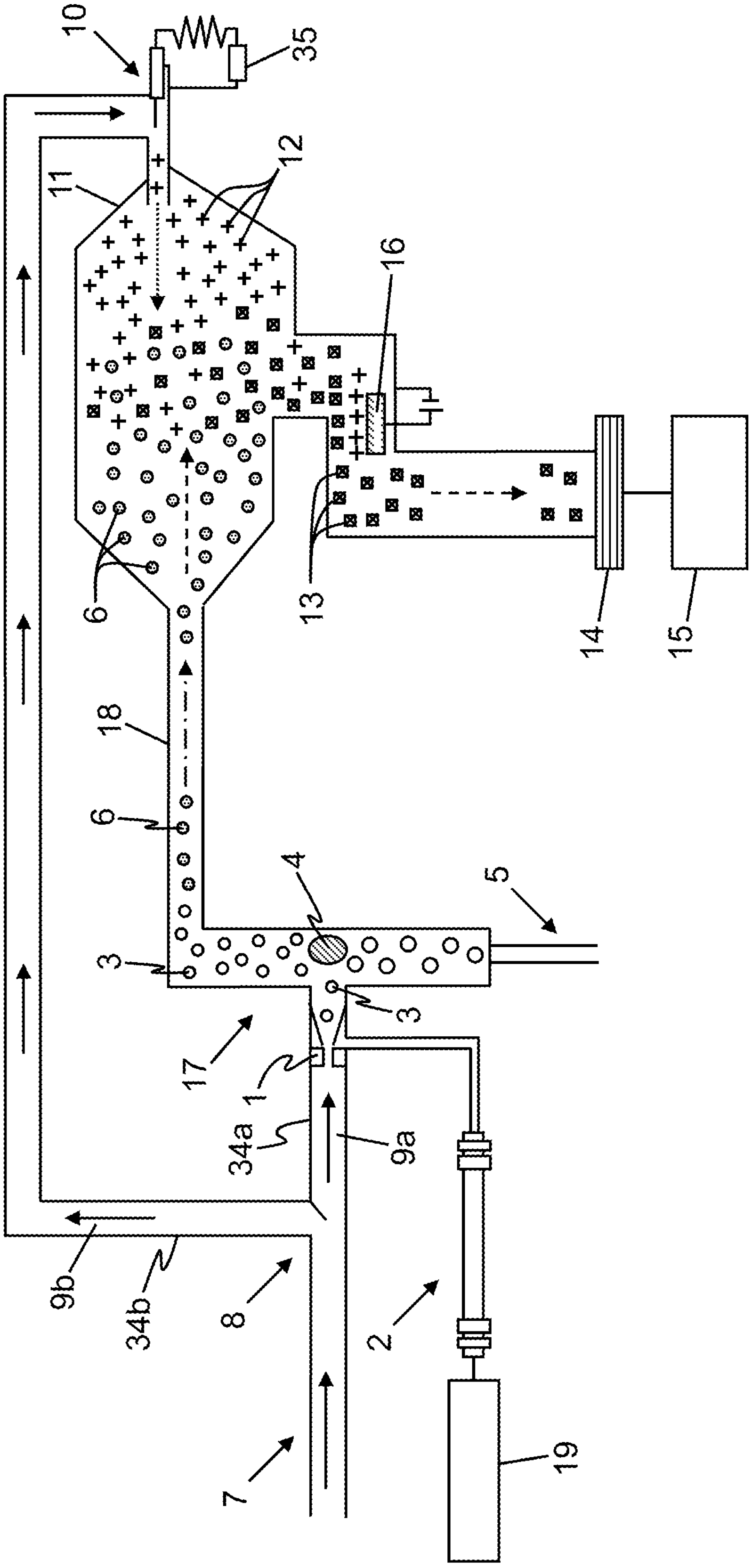
FIG. 1 is a schematic diagram of a conventional charged aerosol detection (CAD) system.

As depicted in FIG. 2, droplets formed at the emitter nozzle 44 travel principally in the horizontal direction (referred to as the major direction) toward back wall 23, as indicated by dashed line 29. The volatile portion of the droplets (e.g., solvent) is evaporated from the droplet surfaces as they traverse the central region, resulting in a reduction in their size and mass. Droplets of sufficiently small size/mass are entrained by the gas flow and negotiate a "hairpin" turn (in which the major direction of droplet travel is substantially reversed within relatively short distance) to pass into upper region 24. The gas flow and entrained droplets (as well as particles of non-volatile analytes formed from fully dried droplets) travel through the upper region from right to left in a major direction substantially reversed with respect to the major direction of droplet travel within central region 22 (as indicated by dashed line 31), and pass thereafter into exit port 28. Evaporation of any residual volatile component continues as the droplets travel through upper region 24. Exit port 28 communicates with a charging chamber (e.g., charging chamber 11 as depicted in FIG. 1) where, as described above, the nonvolatile residue particles are electrically charged for subsequent detection.

The portion of back wall 23 extending upwardly of the medial portion of central region 22 and into upper region 24 is curved, with a relatively large radius of curvature. This geometry assists in maintaining a smooth flow of gas (and the entrained droplets) into upper region 24, and avoids the creation of eddies or other turbulent flow patterns that may adversely affect stability or produce excessive deposition of the droplets or dried particles on the spray chamber walls. The portion of back wall 23 extending downwardly from the medial portion into lower region 26 is preferably gently curved in order to promote the transport of accumulated liquid (resulting from the impact of the larger droplets) to the drain. Relatively large droplets formed in the droplet spray are unable to negotiate the turn into upper region 24 due to their higher momentum, and instead impact the medial portion of back wall 23, as indicated by dashed line 32. The resultant liquid accumulated on back wall 23 flows into lower region 26 under the influence of gravity, and may be continuously or periodically removed therefrom via a drain port (e.g., drain port 5 as illustrated in FIG. 1). The separation of the large droplets eliminates the possibility of incomplete evaporation of volatiles prior to introduction of particles into the charging chamber 11.

Figure 4A:
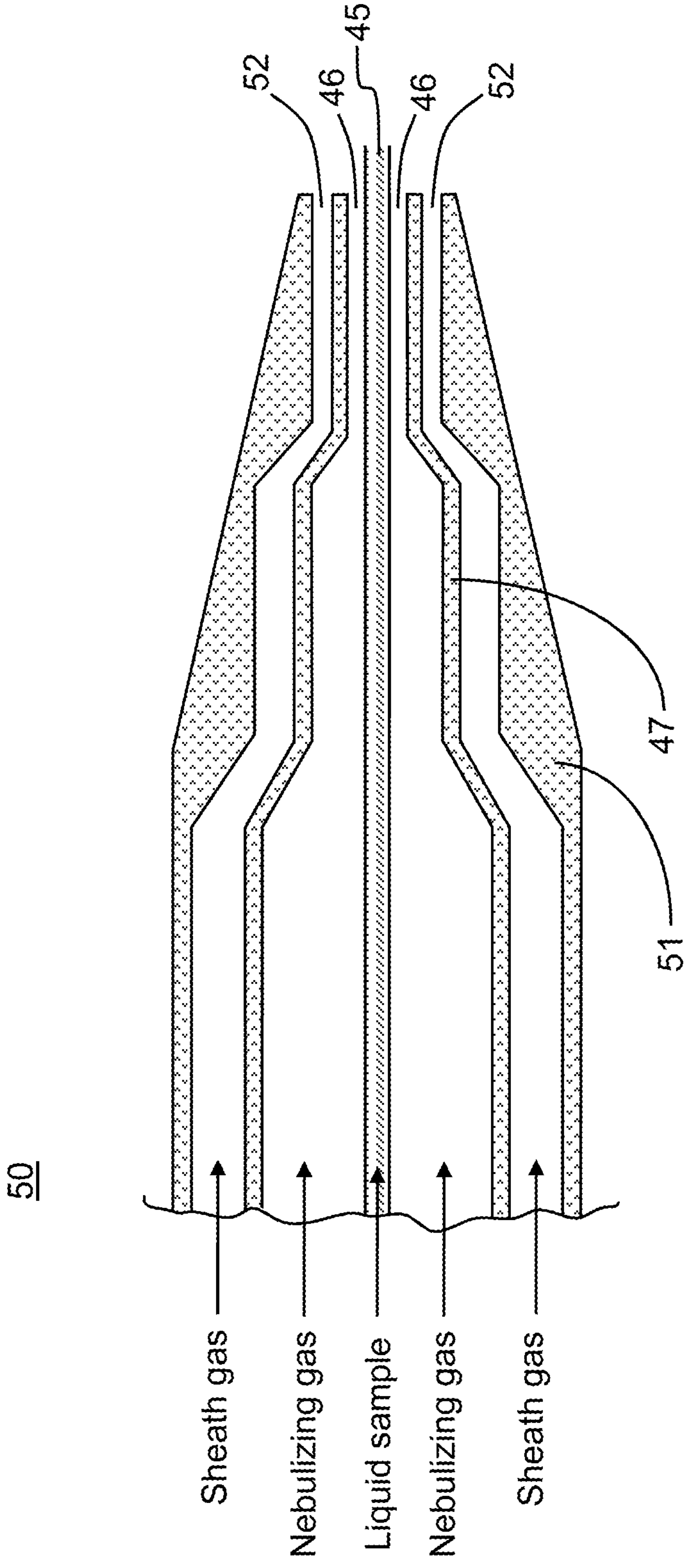
FIG. 4A is a partial cross-sectional view of a spray emitter of a CAD system nebulizer in accordance with the present teachings.

FIG. 4A depicts a partial cross-sectional view of a spray emitter 50 in accordance with the present teachings. The spray emitter 50 illustrated in FIG. 4A is modified with respect to the spray emitter 40 shown in FIG. 3 by provision of a second gas channel 52 which, in operation, carries and emits a second flow of gas (in addition to the nebulizing gas carried by and emitted from conduit 46) whose flow rate is separately controllable independently of the control of nebulizing gas flow rate through conduit 46. The gas that flows through and is emitted from the conduit 52, which may be either of the same composition as or a different composition from the nebulizing gas, is herein referred to as "sheath gas". In the particular exemplary embodiment shown in FIG. 4A, a single sheath gas conduit 52 is provided in a fashion such that the sheath gas conduit concentrically surrounds the nebulizing gas conduit 46 at the spray emitter tip and is separated from the nebulizing gas conduit (such that the two gas flows do not mix internally) by one or more internal walls or partitions 47. The one or more walls or partitions may be supported, in relation to the spray emitter body 51, by one or more ribs, pins or bosses partially spanning the gap created by the conduit 52 or, otherwise, may be contiguous with the emitter body at a not-illustrated location of the spray emitter. The nebulizing gas and sheath gas may be provided to their respective corresponding conduits at separate not-illustrated gas inlet ports.

Although a single nebulizing gas conduit 46 and a single concentrically disposed sheath gas conduit 52 are illustrated in the exemplary embodiment shown in FIG. 4A, each of these individual conduits may be replaced by a single off-axis bore or, preferably a plurality of off-axis bores, each of which carries a portion of the total flow. The sheath gas should be introduced in such a way as to not influence creation and therefore size distribution of the primary aerosol and should also not de-stabilize the spray. Accordingly, it is desirable that the emission of the nebulizing gas, the flow of which is used to effect nebulization, should be in closer proximity to the capillary 45 than the emission of the sheath gas. The sheath and nebulizing gas flow rates should be separately controllable and potentially adjustable in real time where, in most cases, the combined flow rate is held constant. The illustrated configuration of the nebulizing and sheath gas conduits enables adjustment of the primary aerosol characteristics via adjustment of the nebulizer gas flow rate and velocity while maintaining a constant total aerosol gas volumetric flow rate via complementary adjustment of the sheath gas flow rate. For given nebulizer dimensions, a constant velocity through the nebulizer may be maintained.

Figure 4B:
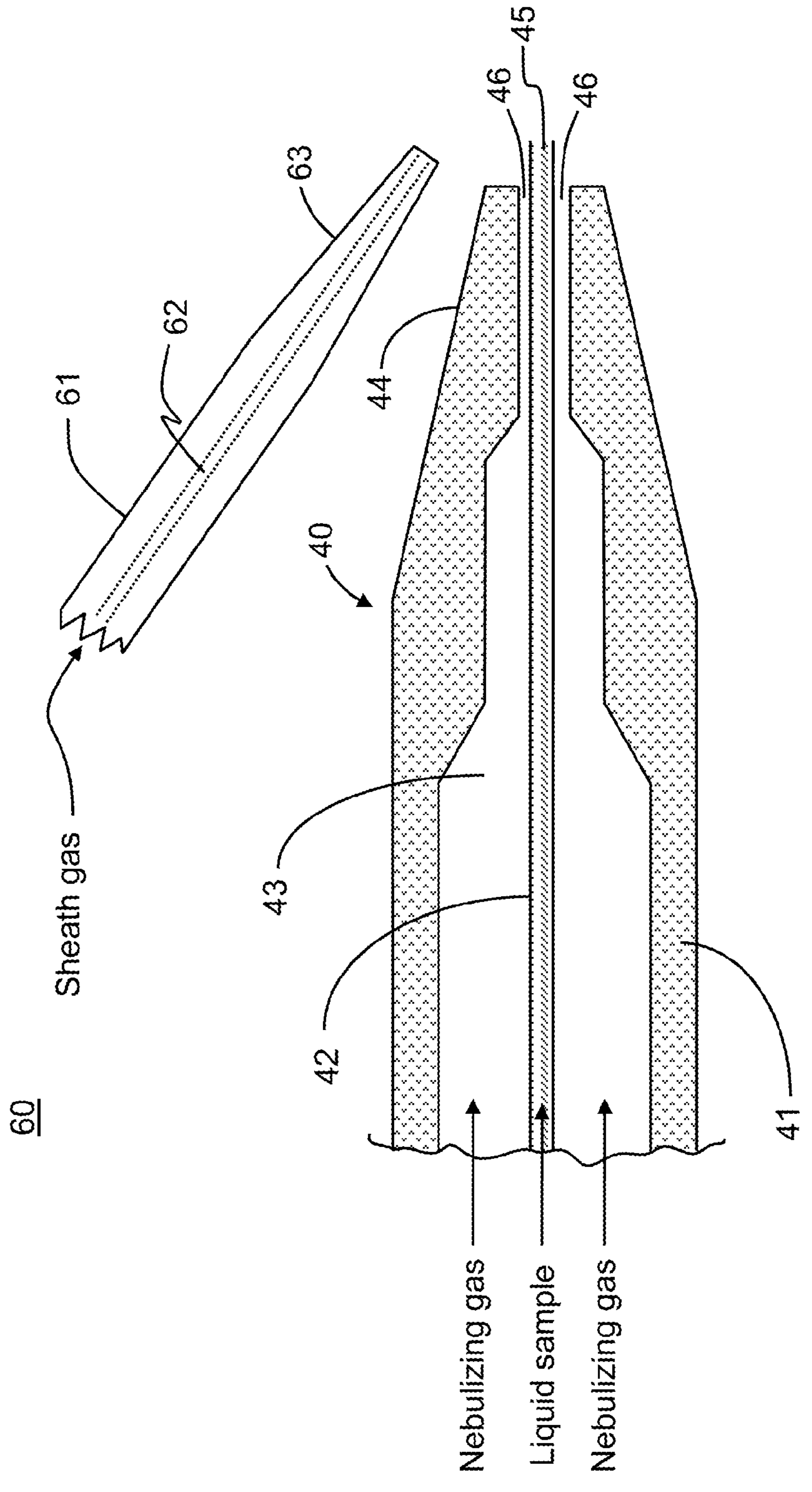
FIG. 4B is a partial cross-sectional view of a spray emitter system of a CAD system nebulizer including a spray emitter and a separate sheath gas emitter.

FIG. 4B illustrates an alternative spray emitter system of a CAD system nebulizer. The system 60 shown in FIG. 4B includes the same spray emitter 40 as illustrated in FIG. 3 and also includes a separate sheath gas emitter 61 that is configured so as to emit a flow of sheath gas in proximity to the emitter tip of the spray emitter 40. The sheath gas emitter may be formed as a tube having one or more internal conduits 62 for provision of the sheath gas and having a nozzle end 63. Although only a single sheath gas emitter is illustrated in FIG. 4B, a plurality of such emitters may be provided so as to, for example, provide multiple sheath gas flows that, together, form a combined sheath gas flow whose emission surrounds the emission of the nebulizing gas and droplet spray. Although the axis of the sheath gas emitter 61 is shown disposed at an angle to the axis of the spray emitter 40, the sheath gas emitter may, in some embodiments, be disposed such that its axis is parallel to the axis of the spray emitter 40 or such that the long dimension of the conduit 62 is parallel the axis of the spray emitter at its emission end. Alternatively, a plurality of such separate sheath gas emitters may be provided so as to surround the spray emitter, such that the axis of each sheath gas emitter is parallel to the axis of the spray emitter or such that the sheath gas conduits 62 are parallel to the axis of the spray emitter at their emission ends.

For a given combination of liquid flow rate, surface tension, viscosity and density, the nebulizer gas flow rate or velocity or the sheath gas flow rate or velocity (or both nebulizer and sheath gas flow rate or velocity) may be adjusted, using the emitter configurations illustrated in FIGS. 4A-4B or modified as discussed above, such that the adjusted nebulizer or sheath gas flow rate or velocity produces a primary aerosol with a desired minimum mean droplet diameter. If the solvent composition of the liquid supplied to the spray emitter varies with time—for example, because it is supplied from gradient-elution chromatography—then the nebulizing or sheath gas flow rate or velocity may be adjusted, using the emitter configurations illustrated in FIGS. 4A-4B or modified as discussed above, so as to provide a mean droplet diameter that does not change with time by more than a predetermined tolerance. For example, Eq. 3 above predicts that a 10 nm dried particle would result from a 2.15 μm primary droplet created from a solution having 100 parts per billion (ppb) of non-volatile solute. Assuming a droplet size distribution that approximately corresponds to a log-normal/2 geometric standard deviation, a primary aerosol with a mean droplet size of approximately 8.6 μm would then be expected to produce a dried aerosol in which more than about 97.5% of the particles have diameters that are greater than 10 nm. Since absolute detector sensitivity to particles having diameter less than or equal to 10 nm particles is lower than that of particles having diameters greater than >10 nm (Eqs. 4a and 4b above), an even higher proportion of smaller droplets and particles might still be tolerated. For example, acceptable results may be expected if more than 50% of the particles in the dried aerosol have diameters that are greater than 10 nm (that is, if the median diameter is greater than 10 nm) or if a geometric mean diameter of the dried particles is greater than 10 nm. In a preferred embodiment, a geometric mean diameter of the dried particles is greater than 15 nm.

Predictive models have been developed (e.g., Kahen et al, "Modified Nukiyama-Tanasawa and Rizk-Lefebvre models to predict droplet size for microconcentric nebulizers with aqueous and organic solvents", J. Anal. At. Spectrom., 2005, 20, pp. 631-637) that provide guidance regarding the relationships between nebulizer dimensions (e.g., gas flow path annular area) and gas flow rate required to produce a given mean droplet diameter. For example, a nebulizer system having components similar to those schematically depicted in the attached FIGS. 2-3 is commercially available from Thermo Fisher Scientific of Waltham, Mass. USA. Using the dimensions of the presently available commercial system (having a nozzle orifice diameter of approximately 450 μm), and a hypothetical liquid flow rate of 0.5 mL/min, an aerosol of approximately 8.6 μm mean droplet diameter would be predicted from nebulizing gas flow rates of about 2.8 and 2.15 L/min, respectively, for water and methanol. Assuming that both solvents contain at least 100 ppb "background" residue (i.e., impurity), then the above conditions should, in theory, consistently produce a dried aerosol in which greater than 97.5% of the particles have particle diameters greater than 10 nm. If the liquid contains less than 100 ppb non-volatile impurity concentration (however unlikely), then a 100 ppb non-volatile analyte concentration would roughly correspond to the instantaneous concentration at peak apex for 10 ng in a 0.1 mL volume of chromatographic liquid.

The above discussion relates to the control of droplet size as the droplets form at a spray emitter. To further ensure that the particles that ultimately are formed from the dried droplets have a suitable size distribution (diameters of most particles greater than 10 nm), it is also desirable to prevent droplets from breaking up into smaller droplets during their transport through the spray chamber and then to the charging chamber 11 through conduit 18. Droplet division may be caused by mechanical breakup as a result of collisions of droplets with surfaces. Some droplet division may be caused by coulombic explosion of charged droplets as charge density increases during solvent evaporation, but this latter process is believed to be less significant than mechanical breakup and may be insignificant in many instances.

Figure 5:
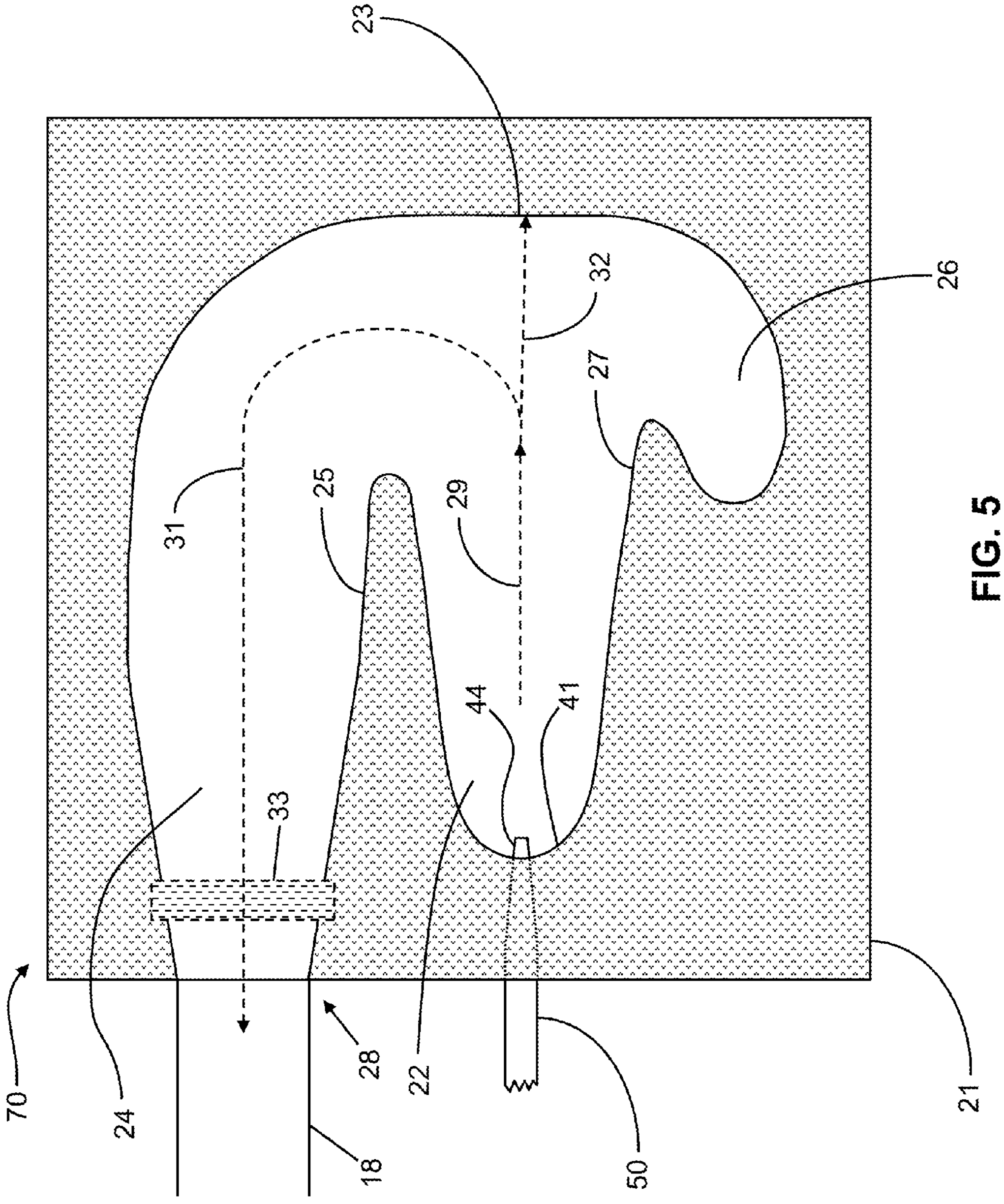
FIG. 5 is a is an elevational cross-sectional view of a first modified CAD system nebulizer, in accordance with the present teachings, depicting the interior of a spray chamber body.
Figure 8:
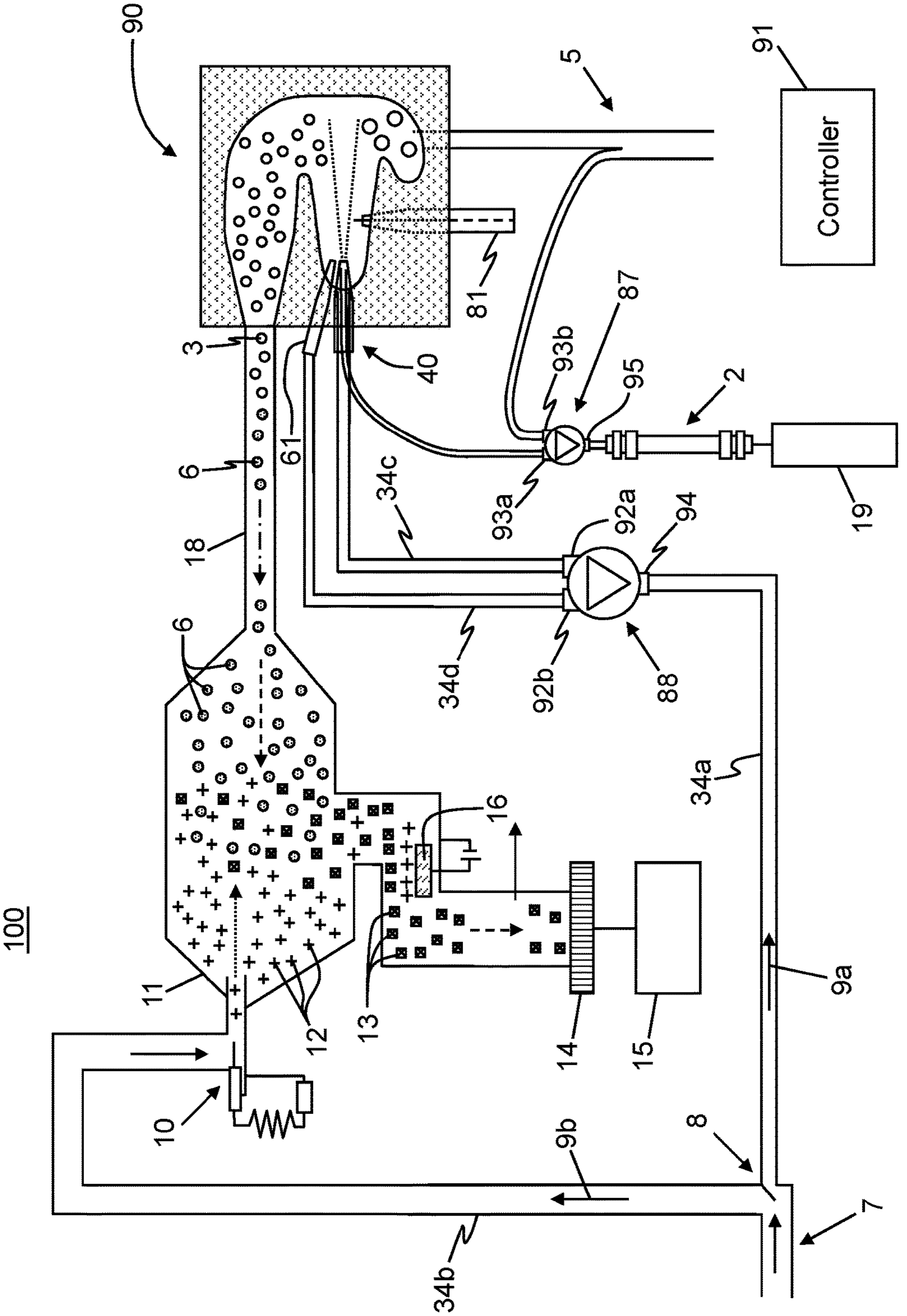
FIG. 8 is a schematic diagram of a CAD system in accordance with the present teachings.

Prevention of mechanical droplet breakup may be achieved by configuring the CAD system as shown in FIG. 8 with a straight path from the nebulizer spray chamber to the charging chamber 11. FIG. 5 depicts an embodiment of a CAD system nebulizer 70 in accordance with the present teachings that facilitates the configuration illustrated in FIG. 8. The interior shape of the spray chamber body of the nebulizer 70 shown in FIG. 5 is modified relative to the nebulizer spray chamber depicted in FIG. 2. However, like elements are referenced by like numbers in both of those figures. In the nebulizer 70, the upper region 24 of the spray chamber interior extends outward to the outer edge of the spray chamber body 21 and opens to the exterior of the spray chamber such that the opening to the exterior comprises the exit port 28. Accordingly, as shown in FIG. 5, the flow of aerosol (gas, droplets and possibly particles) out of the nebulizer is reversed relative to the direction of the initial spray emitted from the spray emitter 50. In alternative embodiments, the flow of aerosol out of the nebulizer is not exactly reversed relative to the direction of the initial spray and may be at any arbitrary direction.

A diffusion screen 33 may be optionally included in the aerosol pathway so as to remove any remaining small droplets, which would give rise to particles having particle diameters less than or equal to 10 nm. In the example shown in FIG. 5, the diffusion screen is installed in the spray chamber interior so as to remove droplets. Alternatively, the diffusion screen may be installed downstream within the conduit 18 so as to remove solid particles formed by drying of the droplets. As is known, the diffusion screen may comprise a wire mesh designed such that smaller droplets or particles with higher mobility (e.g., Brownian motion) have higher probability of colliding with the solid wire structure.

Figure 6:
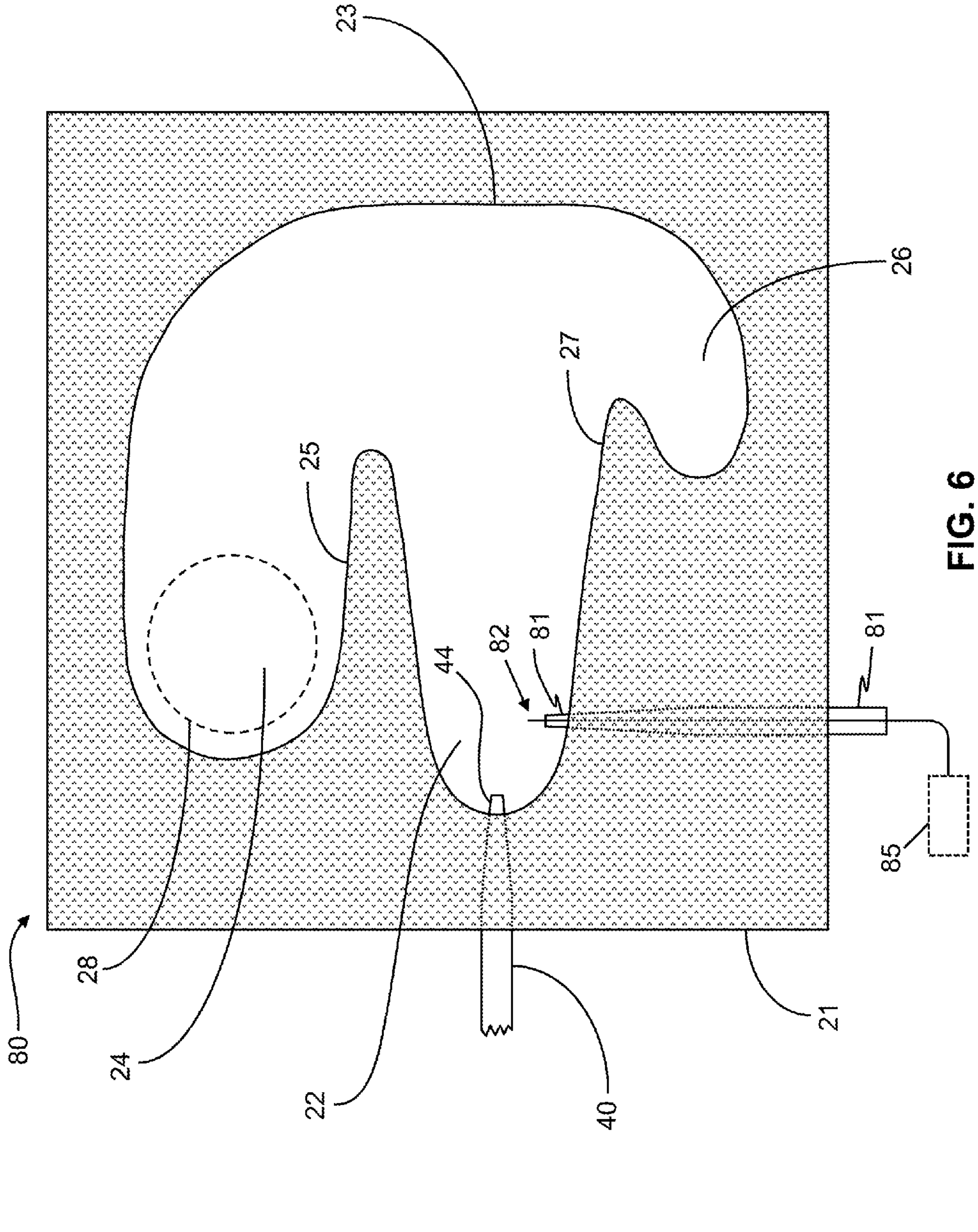
FIG. 6 is a is an elevational cross-sectional view of a second modified CAD system nebulizer in accordance with the present teachings.
Figure 7:
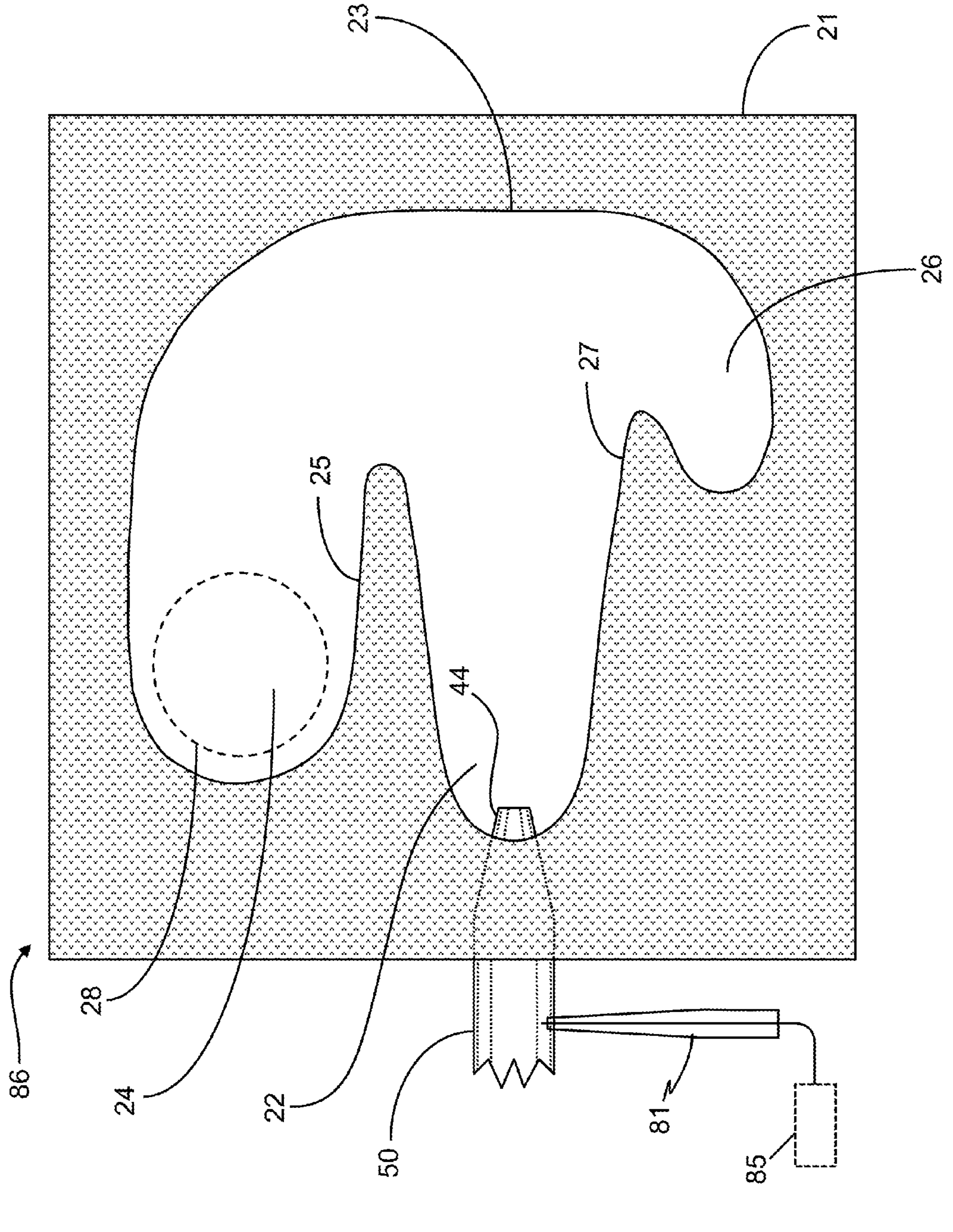
FIG. 7 is a is an elevational cross-sectional view of a third modified CAD system nebulizer in accordance with the present teachings.

FIG. 6 is an elevational cross-sectional view of a second modified CAD system nebulizer 80 in accordance with the present teachings. The nebulizer 80 includes an ion source 81 in proximity to the emitter tip of the spray emitter 40 (or, alternatively, the emitter 50 or the emitter system 60) that provides ions that neutralize any charge acquired by droplets during their formation at the emitter tip. The neutralization of droplet charge in this fashion may prevent droplet division by coulombic explosion and the consequent reduction of average droplet diameter in the event that natural droplet electrification occurs (although this process is believed to be generally insignificant). The ion source may, according to some embodiments, be provided as a radioactive source of α-particles or β-particles or as a source of ionizing radiation, such as X-rays. In accordance with some embodiments and the illustrative drawing provided in FIG. 6, the source of ions may be provided as a corona discharge needle 82 which is maintained at high voltage value (or at a plurality of high voltage values) by a voltage source 85. The corona discharge needle 82 may be maintained at a constant polarity (e.g., a DC voltage) or may be provided with alternating positive and negative polarities (e.g., an AC voltage) so as to neutralize, respectively, both negatively and positively charged droplets. FIG. 7 is a schematic diagram of another nebulizer for a CAD system in accordance with the present teachings. The nebulizer 86 shown in FIG. 7 differs from the nebulizer 80 of FIG. 6 in that, in the nebulizer 86, the ion source is provided in contact with the sheath gas flow within a spray emitter 50 (see FIG. 4A) or, alternatively, in contact with the sheath gas flow within a separate sheath gas emitter 61 (see FIG. 4B).

FIG. 8 is a schematic diagram of a CAD system 100 in accordance with the present teachings. The CAD system 100 includes a nebulizer 90 that may include any or all of the nebulizer features, either alone or in combination, that are depicted in FIGS. 4A, 4B, 5, 6 and 7 and discussed above. As illustrated, the nebulizer 90 includes a spray chamber design (see FIG. 5) in which the upper region 24 of the spray chamber interior extends outward to the outer edge of the spray chamber body 21 and opens to the exterior of the spray chamber such that the opening to the exterior comprises the exit port 28. Using such a design, taken in conjunction with the configuration of components as illustrated in FIG. 8, the nebulizing gas and entrained droplets and particles flow along a straight path through the conduit 18 that fluidically interconnects the nebulizer 90 with the charging chamber 11. In this fashion, any collision of already formed droplets with the walls of the spray chamber of the nebulizer 90 or with the walls of conduit 18 are minimized, thereby minimizing transport-induced reduction of average droplet size.

The CAD system 100 further includes a liquid flow splitter 87, which may be provided as a proportional valve having a fluid inlet port 95 and two fluid outlet ports 93*a*, 93*b*, that receives a flow of eluate from an outlet port of a chromatographic column 2 and divides the eluate into a first portion that is directed to a spray emitter (e.g., spray emitter 40, as shown in FIG. 8) through first splitter outlet port 93*a* and a second portion that is directed to drain port 5 through second splitter outlet port 93*b*. The function of the liquid flow splitter 87 is to split the liquid flow prior to the introduction of the first portion to the nebulizer 90 so as to reduce the solvent load within the nebulizer to a level where evaporation and aerosol transport efficiency of water can approach 100%. This operation preferably employs a liquid flow splitter that is mostly independent of solvent viscosity. In that way the total volume of liquid and therefore mass of non-volatile solute reaching the detector may be maintained independent of solvent properties. Thus, according to some embodiments, any change in volumetric flow rate that is dispensed from the outlet port of the chromatographic column or that is otherwise received by the spray emitter, possibly as a result of changing eluent viscosity or density during gradient elution, may be taken up by the portion of the flow directed to the drain port 5. According to other embodiments, the split proportions may be adjusted during elution, perhaps automatically under programmatic control, so as to main a constant chemical activity of water in the eluate and, consequently, a constant water vapor fugacity within the spray chamber. In order to further normalize detector response of the CAD system 100, concurrent nebulizer or sheath gas flow adjustments (or both) may be implemented so as to maintain a similar primary aerosol size distribution throughout a solvent gradient separation as the viscosity of the eluent changes.

As illustrated, the CAD system 100 further includes a gas flow splitter 88 having an inlet port 94 and first and second outlet ports 92*a*, 92*b*. The gas flow splitter 88 is disposed so as to receive the flow portion 9*a* of gas that is provided from gas conduit 34*a* (cf., FIG. 1) and to further split this gaseous flow into a nebulizing gas portion that is delivered to gas conduit 34*c* through first outlet port 92*a* and a sheath gas portion that is delivered to gas conduit 34*d* through second outlet port 92*b*. As illustrated in FIG. 8, the nebulizing gas portion is provided to a spray emitter 40 and the sheath gas portion is provided to a separate sheath gas emitter 61 (or to a plurality of such emitters) as discussed above with reference to FIG. 4B. Alternatively, the nebulizing gas may be provided to a nebulizing gas channel of a spray emitter 50 and the sheath gas may be provided to a sheath gas channel 52 of the same spray emitter, as discussed above with reference to FIG. 4A. The gas flow splitter 88 may adjust the split proportions during elution, perhaps automatically under programmatic control, so as to maintain constant droplet size. A programmable electronic controller 91 may be electronically coupled to the gas flow splitter 88 and/or to the liquid flow splitter 87. The programmable electronic controller may be configured to vary relative proportions of gas flow output by the first and second outlet ports 92*a*. 92*b* of the gas flow splitter 88 in accordance with a varying solvent composition or to vary relative proportions of liquid flow output by the first and second outlet ports 93*a*, 93*b* of the liquid flow splitter 87 in accordance with a varying eluent composition. The inventor has found that, in practice, good results may be obtained by varying the sheath gas flow while keeping the nebulizer gas constant. The preferred approach includes a decrease in sheath gas flow with increasing percentage of organic components of the fluid delivered to the CAD system. This approach is believed to facilitate increased transport of aerosols derived from more-aqueous solvents (that is, lower percentages of organic components). As discussed above, a liquid flow splitter (component 87) is employed. One function of the splitter is to allow capillary-derived flow rates through the nebulizer while receiving much greater effluent flow rates from an analytical scale liquid chromatograph.

Figure 9A:
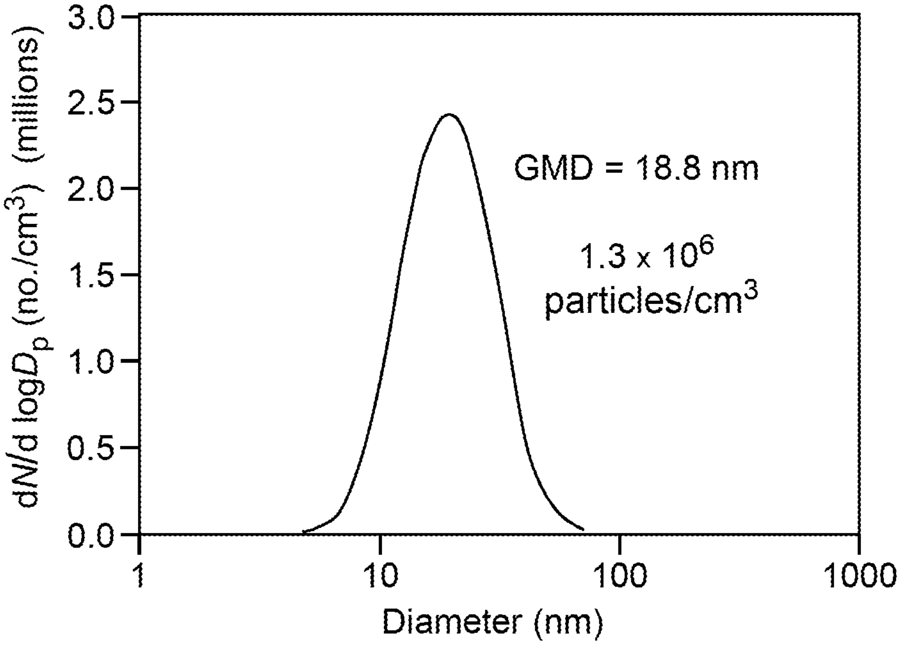
FIG. 9A is a smoothed plot of particle size distribution, as measured by a scanning mobility particle sizer at the outlet of a charged aerosol detection apparatus in accordance with the present teachings for a continuous 1.0 mL/min inlet flow of 1.0 μg/mL theophylline in 20% v/v aqueous $CH_3OH$.
Figure 9B:
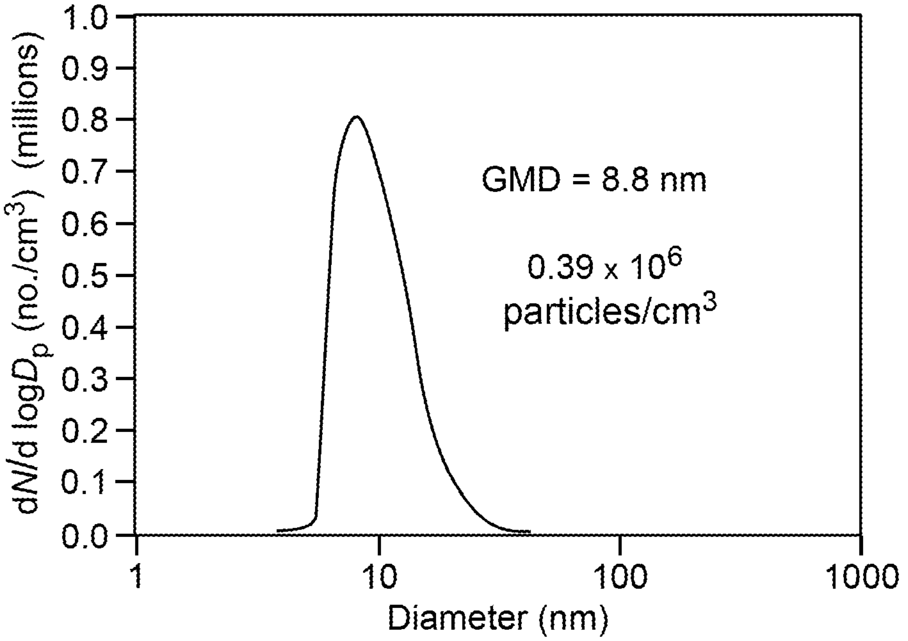
FIG. 9B is a smoothed plot of particle size distribution, as measured by a scanning mobility particle sizer at the outlet of a conventional charged aerosol detection apparatus for a continuous 1.0 mL/min inlet flow of 1.0 μg/mL theophylline in 20% v/v aqueous $CH_3OH$.

It is believed that charged aerosol detection systems in accordance with the present teachings provide an advantageous reduction in the relative proportion of small particles (for example, particle diameters of ≤10 nm), relative to conventional CAD systems. Evidence in support of this belief is provided in FIGS. 9A-9B, which compare particle size distributions, as measured by a scanning mobility particle sizer at the outlet of a CAD system in accordance with the present teachings (FIG. 9A) and at the outlet of a prior-design CAD system (FIG. 9B). The data used to produce the plots shown in FIGS. 9A and 9B was, in both instances, obtained by providing a constant 1.0 mL/min flow of 1.0 μg/mL theophylline in 20% v/v aqueous $CH_3OH$ to the respective CAD system. FIGS. 9A-9B illustrate that, for the same solution concentration and flow rate, the new design in accordance with the present teachings produces a dried aerosol distribution with a significantly larger mean particle size and number concentration (specifically, a geometric mean diameter of 18.8 nm and a number concentration of $1.3\times10^6$ per $cm^3$) than does the prior-design system (geometric mean diameter of 8.8 nm and number concentration of $0.39\times10^6$ per $cm^3$). Although the prior-design CAD system is expected to produce a course (i.e., large characteristic droplet size) primary aerosol, the impactor design and location that is employed in that system imposes a particle size distribution that is shifted towards smaller values.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the scope and essence of the invention. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A system for detection and measurement of a non-volatile solute having density ρ in its condensed form that is dissolved in a liquid solvent at a concentration C, the system comprising:

- a spray emitter system configured to receive a flow of liquid solution comprising the solvent and dissolved solute and to generate an aerosol comprising droplets of the liquid solution, wherein the generated droplets comprise an initial size distribution wherein greater than 50 percent of the droplets have diameters, in units of nanometers, that are greater than $10\times(C/\rho)^{-1/3}$, where C and ρ are expressed in identical units;
- a spray chamber configured to receive the aerosol and to modify the initial size distribution of the aerosol droplets by eliminating liquid droplets having diameters greater than a maximum droplet diameter that is greater than $10\times(C/\rho)^{-1/3}$;
- a conduit configured to receive a flow of the aerosol having the modified size distribution from the spray chamber and to cause evaporation of the solvent from the received liquid droplets so as to generate a further modified aerosol consisting essentially of the carrier gas and residue particles of the non-volatile solutes;

a charging chamber configured to receive the further modified aerosol from the conduit and to impart electric charge to the residue particles thereof; and a detector configured to receive the charged residue particles from the charging chamber and to measure a quantity of charge imparted to the residue particles, wherein the modification of the initial size distribution of aerosol droplets is such that greater than 50 percent of the charged residue particles received by the detector have particle diameters greater than 10 nm.

2. A system as recited in claim 1, wherein the spray emitter system comprises:

a capillary having an outlet end configured to provide the flow of the liquid solution into the spray chamber;

at least one nebulizing gas conduit having an outlet end configured to provide a flow of nebulizing gas into the spray chamber; and at least one sheath gas conduit having an outlet end configured to provide a flow of sheath gas into the spray chamber, wherein the flow of nebulizing gas into the spray chamber is provided in closer proximity to the capillary outlet end than is the flow of sheath gas.

3. A system as recited in claim 2, wherein the nebulizing gas conduit consists of a single conduit circumferentially surrounding the capillary at the capillary outlet end and the sheath gas conduit consists of a single conduit circumferentially surrounding the nebulizing gas conduit at the nebulizing gas conduit outlet end.

4. A system as recited in claim 2, wherein the flow of the liquid solution and the flow of the nebulizing gas are provided from a first tube and the flow of the sheath gas is provided from at least one other tube.

5. A system as recited in claim 4, wherein the at least one other tube comprises a plurality of other tubes circumferentially surrounding the first tube.

6. A system as recited in claim 2, wherein flow axes of the flow of the liquid solution, the flow of the nebulizing gas and the flow of the sheath gas are substantially co-directional.

7. A system as recited in claim 1, further comprising:

a gas flow splitter comprising:

an inlet port fluidically coupled to a gas source;

a first outlet port fluidically coupled to the nebulizing gas conduit; and a second outlet port fluidically coupled to the sheath gas conduit.

8. A system as recited in claim 7, further comprising:

a chromatographic column configured to provide the flow of liquid solution to the spray emitter such that the liquid solvent varies in chemical composition with time; and a programmable electronic controller electronically coupled to the gas flow splitter, wherein the programmable electronic controller is configured to vary relative proportions of gas flow output by the first and second outlet ports in accordance the varying solvent composition.

9. A system as recited in claim 1, further comprising:

a chromatographic column configured to provide a flow of a liquid eluate, said liquid eluate comprising the liquid solution.

10. A system as recited in claim 9, further comprising:

a liquid flow splitter comprising:

an inlet port fluidically coupled to the chromatographic column so as to receive the eluate therefrom;

a first outlet port fluidically coupled to the spray emitter system; and a second outlet port fluidically coupled to a drain or waste line; and a programmable electronic controller electronically coupled to the liquid flow splitter, wherein the programmable electronic controller is configured to vary relative proportions of liquid flow output by the first and second outlet ports in accordance a varying chemical composition of an eluent portion of the eluate.

11. A system as recited in claim 1, wherein:

the spray chamber has a central region into which the aerosol is introduced and a rear surface positioned opposite an outlet of the spray emitter, the spray chamber including a partition dividing the central region from an upper region and defining a passageway between the central and upper regions through which a portion of the droplets in the aerosol travel, the upper region communicating with an exit of the spray chamber, and a major direction of droplet travel within the upper region is substantially reversed with respect to the major direction of droplet travel within the central region such that droplets within the aerosol having a diameter larger than the maximum droplet diameter are unable to negotiate the passageway from the central to the upper region and impact the rear surface.

12. A method for detecting and measuring a non-volatile solute having density ρ in its condensed form that is dissolved in a liquid solution comprising a liquid solvent at a concentration C, the method comprising:

generating an aerosol of droplets of the liquid solution, wherein the generated droplets comprise an initial size distribution wherein greater than 50 percent of the droplets have diameters, in units of nanometers, that are greater than $10\times(C/\rho)^{-1/3}$, where C and ρ are expressed in identical units;

transporting a portion of the droplets to a charging chamber through one or more conduits such that division of the portion of the droplets into smaller droplets within the one or more conduits is inhibited and such that the solvent fully evaporates during the transporting so as to generate a plurality of solid particles from the droplets of the portion of droplets;

imparting electric charge to the solid particles in the charging chamber; and measuring a quantity of charge imparted to the solid particles by a detector, wherein initial size distribution and the inhibition of droplet division are such that particles having diameters greater than 10 nm comprise more than 50 percent of all particles received by the detector.

13. A method as recited in claim 12, wherein the generation of the aerosol of droplets of the liquid solution comprises:

emitting a spray of the solution from a tip of a capillary into a spray chamber;

emitting a flow of a nebulizing gas into the spray chamber from a nebulizing gas conduit having an outlet in proximity to the capillary tip; and emitting a flow of a sheath gas into the spray chamber from a sheath gas conduit having an outlet in proximity to the outlet of the nebulizing gas conduit, wherein a rate of flow of the emitted nebulizing gas is variable and dependent upon density, viscosity and surface tension of the solution such that the generated droplets comprise the initial size distribution, and wherein a combined rate of flow of the nebulizing gas and the sheath gas is invariant with the density, viscosity and surface tension of the solution.

14. A method as recited in claim 13, wherein the emitting of the nebulizing gas flow is such that the emitted nebulizing gas circumferentially surrounds the capillary tip.

15. A method as recited in claim 14, wherein the emitting of the sheath gas flow is such that the emitted sheath gas circumferentially surrounds the outlet of the nebulizing gas conduit.

16. A method as recited in claim 12, wherein the transporting of the portion of the droplets through the one or more conduits comprises:

transporting the generated droplets through a conduit in a spray chamber such that droplets having a diameter greater than or equal to a maximum value are removed by collision with a wall of the spray chamber, wherein the non-removed droplets include the portion of the droplets; and transporting the non-removed droplets though a transport conduit that forms a straight path between an outlet port of the spray chamber and an inlet port of the charging chamber.

17. A method as recited in claim 12, wherein the transporting of the portion of the droplets through the one or more conduits comprises controlling a variable flow rate of the portion of the droplets through the one or more conduits in accordance with a varying chemical composition of the liquid solvent such that the solvent fully evaporates during the transporting.

18. A method as recited in claim 17, wherein the controlling of the variable flow rate of the portion of the droplets comprises controlling a variable flow rate of the liquid solution to a point at which the aerosol of droplets is generated in accordance with the varying chemical composition of the liquid solvent.

19. A method as recited in claim 12, wherein the transporting of the portion of the droplets through the one or more conduits comprises:

transporting the generated droplets through a conduit in a spray chamber such that droplets having a diameter greater than or equal to a predetermined value are removed by collision with a wall of the spray chamber, wherein the non-removed droplets include the portion of the droplets; and transporting the non-removed droplets though a transport conduit that that is fluidically coupled between an outlet port of the spray chamber and an inlet port of the charging chamber, wherein the transport conduit comprises a non-straight cylindrical tube having a radius and wherein no bend of the conduit comprises a radius of curvature that is less than five times the radius of the transport conduit radius.

20. A method as recited in claim 19, wherein the transporting of the portion of the droplets through the one or more conduits comprises controlling a variable flow rate of the portion of the droplets through the one or more conduits in accordance with a varying chemical composition of the liquid solvent such that the solvent fully evaporates during the transporting.

21. A method as recited in claim 20, wherein the controlling of the variable flow rate of the portion of the droplets comprises controlling a variable flow rate of the liquid solution to a point at which the aerosol of droplets is generated in accordance with the varying chemical composition of the liquid solvent.

22. A method as recited in claim 12, wherein the transporting of the portion of the droplets through the one or more conduits comprises neutralizing charged droplets by exposure of the droplets to ions within the one or more conduits.

23. A method for detecting and measuring a non-volatile solute that is dissolved in a liquid solution comprising a liquid solvent comprising:

generating an aerosol of droplets of the liquid solution;

transporting a portion of the droplets to a charging chamber through one or more conduits comprising a diffusion screen that preferentially removes, from the portion of the droplets, droplets having diameters less than a minimum diameter, wherein the transporting is such that the solvent fully evaporates during the transporting so as to generate a plurality of solid particles from the non-removed droplets;

imparting electric charge to the solid particles within the charging chamber; and measuring a quantity of charge imparted to the solid particles by a detector, wherein the removal of droplets by the diffusion screen is such that particles having diameters greater than 10 nm comprise more than 50 percent of all particles received by the detector.

* * * * *

UNITED STATES PATENT AND TRADEMARK OFFICE
CERTIFICATE OF CORRECTION

PATENT NO. : 10,429,366 B2
APPLICATION NO. : 15/189798
DATED : October 1, 2019
INVENTOR(S) : Paul Gamache It is certified that error appears in the above-identified patent and that said Letters Patent is hereby corrected as shown below:

In the Claims

Claim 8, Column 17, Line 62:
Replace "outlet ports in accordance the"
With --outlet ports in accordance with the--

Claim 10, Column 18, Line 13:
Replace "outlet ports in accordance"
With --outlet ports in accordance with--

Claim 16, Column 19, Line 27:
Replace "transporting the non-removed droplets though a transport"
With --transporting the non-removed droplets through a transport--

Claim 19, Column 20, Line 4:
Replace "transporting the non-removed droplets though a transport"
With --transporting the non-removed droplets through a transport--

Claim 19, Column 20, Line 5:
Replace "conduit that that is fluidically coupled"
With --conduit that is fluidically coupled--

Signed and Sealed this
Twenty-fourth Day of March, 2020

Andrei Iancu
*Director of the United States Patent and Trademark Office*